United States Patent [19]

Stahlheber

[11] 3,965,169

[45] June 22, 1976

[54] CRYSTALLINE TRISODIUM CARBOXYMETHYLOXYSUCCINATE MONOHYDRATE

[75] Inventor: N. Earl Stahlheber, Columbia, Ill.

[73] Assignee: Monsanto Company, St. Louis, Mo.

[22] Filed: Feb. 25, 1974

[21] Appl. No.: 445,693

[52] U.S. Cl. .................. 260/535 P; 252/DIG. 1; 252/DIG. 10; 252/DIG. 11
[51] Int. Cl.² ..................................... C07C 59/22
[58] Field of Search .......................... 260/535 P

[56] References Cited

UNITED STATES PATENTS 3,692,685  9/1972  Lamberti et al. .............. 260/535 P

*Primary Examiner*—Paul J. Killos
*Attorney, Agent, or Firm*—J. E. Maurer; N. E. Willis; T. N. Wallin

[57] ABSTRACT

Trisodium carboxymethyloxysuccinate monohydrate is useful as a metal complexing agent, detergency builder and desiccant.

1 Claim, No Drawings

CRYSTALLINE TRISODIUM CARBOXYMETHYLOXYSUCCINATE MONOHYDRATE

BACKGROUND OF THE INVENTION

This invention relates to a novel compound useful as a metal complexing agent, detergency builder and desiccant.

It is known that trisodium carboxymethyloxysuccinate is an effective metal complexing agent and detergency builder. This material in its anhydrous form is non-crystalline and readily takes up water from humid atmospheres, thereby exhibiting an undesirable tendency to cake or agglomerate. The water uptake continues until sufficient water is present to permit spontaneous crystallization of tetra or penta hydrate forms of the material. The tetra and penta hydrates of trisodium carboxymethyloxysuccinate are crystalline, relatively non-hygroscopic materials which can be easily handled under humid atmospheres without agglomerating or caking. However, the high moisture content of these hydrates (greater than 20% by weight) renders the shipping of the tetra and penta hydrate forms relatively uneconomical.

Thus, it is apparent that materials which exhibit the desirable functional characteristics of trisodium carboxymethyloxysuccinate without the caking and agglomeration problems associated with the anhydrous form thereof, and without the shipping cost associated with forms containing large amounts of water such as the penta and tetra hydrates would constitute a significant advance in the art.

SUMMARY OF THE INVENTION

It is an object of this invention to provide a novel material having the functional characteristics of trisodium carboxymethyloxysuccinate and which is relatively free from tendencies to cake or agglomerate and which is associated with relatively low amounts of inert materials such as water.

The objects of the invention are obtained by means of a novel compound, trisodium carboxymethyloxysuccinate monohydrate whose manufacture, use and characteristics will be understood from the following description of the preferred embodiments.

DESCRIPTION OF THE PREFERRED EMBODIMENTS

The compound of this invention is trisodium carboxymethyloxysuccinate monohydrate which can be represented by the formula

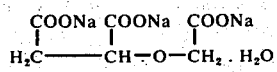

This compound can be prepared by forming a mixture containing 8% to 15% water and 92% to 85% trisodium carboxymethyloxysuccinate by weight, and crystallizing trisodium carboxymethyloxysuccinate monohydrate from the mixture at temperatures above 112°C. Generally, temperatures in the range of about 120°C are required to effect solution of the carboxymethyloxysuccinate in the amount of water indicated. Preferably, the solution is formed by heating in a closed system since in an open system water tends to be driven off before the stable crystalline monohydrate is formed. Crystallization can be effected by lowering the temperatures and is facilitated by conventional techniques such as stirring and/or seeding. The temperature should not be lowered below 112°C until crystallization is substantially complete and excess water is removed in order to prevent formation of higher hydrates.

After crystallization is complete, the pressure on the system can be released to effect drying of the monohydrate which does not lose its water of hydration at temperatures below about 160° to 200°C.

The existence of trisodium carboxymethyloxysuccinate monohydrate is quite unexpected. If anhydrous trisodium carboxymethyloxysuccinate is exposed to a humid atmosphere, the material is observed to become quite "tacky" through moisture take up and periodic X-ray diffraction analysis does not reveal the presence of any crystalline structure until sufficient moisture is present to permit formation of the tetra and/or penta hydrates.

The physical properties of trisodium carboxymethyloxysuccinate monohydrate are also surprisingly different from those of the anhydrous material and its penta and tetra hydrates.

Although the monohydrate will readily take up water from a humid atmosphere and, when sufficient water is present, form the relatively non-hygroscopic tetra and/or penta hydrates, unlike the anhydrous material it does not become tacky or cake or agglomerate during this process. This property renders the monohydrate useful as a desiccant and as a water sink in detergent formulations or other compositions containing materials which tend to cake in a humid atmosphere. That is, the monohydrate not only is free from caking and agglomeration tendencies, but serves to remove excess moisture and thereby prevent caking of other materials with which it is associated.

As previously mentioned, the monohydrate retains its water of hydration up to temperatures of 160° to 200°C whereas the tetra and penta hydrates lose water of hydration at about 112°C. The monohydrate can be used in detergent formulations as a builder, in the same manner as the anhydrous material, but without the tackiness and pronounced caking tendency of the anhydrous material.

The detergent formulations will contain at least 1% by weight and preferably at least 5% by weight of the monohydrate of this invention. In order to obtain the maximum advantages of the builder compositions of this invention, the use of from 5% to 75% of this monohydrate is particularly preferred. The monohydrate compound of this invention can be the sole detergency builder or this compound can be utilized in combination with other detergency builders which may constitute from 0 to 95% by weight of the total builders in the formulation. By way of example, builders which can be employed in combination with the novel builder compounds of this invention include water soluble inorganic builder salts such as alkali metal polyphosphates, i.e., the tripolyphosphates and pyrophosphates, alkali metal carbonates, borates, bicarbonates and silicates and water soluble organic builders including amino polycarboxylic acids and salts such as alkali metal nitrilotriacetates, cycloalkane polycarboxylic acids and salts, other ether polycarboxylates, alkyl polycarboxylates, epoxy polycarboxylates, tetrahydrofuran polycarboxylates such as 1,2,3,4 or 2,2,5,5 tetrahydrofuran tetracarboxylates, benzene polycarboxylates, oxidized starches, amino (trimethylene phosphonic acid) and its salts, diphosphonic acids and salts (e.g., methylene diphosphonic acid; 1-hydroxy ethylidene diphosphonic acid) and the like, as well as anhydrous tetrasodium carboxymethyloxysuccinate and the tetra and penta hydrates thereof.

The detergent formulations will generally contain from 5% to 95% by weight total builder (although greater or lesser quantities may be employed if desired) which, as indicated above, may be solely the monohydrate compound of this invention or mixtures of such compound with other builders. The total amount of builder employed will be dependent on the intended use of the detergent formulation, other ingredients of the formulation, pH conditions and the like. For example, general laundry powder formulations will usually contain 20% to 60% builder; liquid dishwashing formulations 11% to 12% builder; machine dishwashing formulations 60% to 90% builder. Optimum levels of builder content as well as optimum mixtures of builders of this invention with other builders for various uses can be determined by routine tests in accordance with conventional detergent formulation practice.

The detergent formulations will generally contain a water soluble detergent surfactant although the surfactant ingredient may be omitted from machine dishwashing formulations. Any water soluble anionic, non-ionic, zwitterionic or amphoteric surfactant can be employed.

Examples of suitable anionic surfactants include soaps such as the salts of fatty acids containing about 9 to 20 carbon atoms, e.g., salts of fatty acids derived from coconut oil and tallow; alkyl benzene sulfonates—particularly linear alkyl benzene sulfonates in which the alkyl group contains from 10 to 16 carbon atoms; alcohol sulfates; ethoxylated alcohol sulfates; hydroxy alkyl sulfonates; alkyl sulfates and sulfonates; olefin sulfonates; alkenyl sulfonates; monoglyceride sulfates; acid condensates of fatty acid chlorides with hydroxy alkyl sulfonates and the like.

Examples of suitable nonionic surfactants include alkylene oxide (e.g., ethylene oxide) condensates of mono and polyhydroxy alcohols, alkyl phenols, fatty acid amides, and fatty amines; amine oxides; sugar derivatives such as sucrose monopalmitate; long chain tertiary phosphine oxides; dialkyl sulfoxides; fatty acid amides, (e.g. mono or diethanol amides of fatty acids containing 10 to 18 carbon atoms), and the like.

Examples of suitable zwitterionic surfactants include derivatives of aliphatic quaternary ammonium compounds such as 3-(N,N-dimethyl-N-hexadecylammonio) propane-1-sulfonate and 3-(N,N-dimethyl-N-hexadecylammonio)-2-hydroxy propane-1-sulfonate.

Examples of suitable amphoteric surfactants include betains, sulfobetains and fatty acid imidazole carboxylates and sulfonates.

It will be understood that the above examples of surfactants are by no means comprehensive and that numerous other surfactants are known to those skilled in the art. It will be further understood that the choice and use of surfactants will be in accordance with well understood practices of detergent formulations. For example, anionic surfactants, particularly linear alkyl benzene sulfonate are preferred for use in general laundry formulations, whereas low foaming nonionic surfactants are preferred for use in machine dishwashing formulations.

The quantity of surfactant employed in the detergent formulations will depend on the surfactant chosen and the end use of the formulation. In general, the formulations will contain from 5% to 50% surfactant by weight, although as much as 95% or more surfactant may be employed if desired. For example, general laundry powder formulations normally contain 5% to 50%, preferably 15% to 25% surfactant; machine dishwashing formulations, .5% to 5%; liquid dishwashing formulations 20% to 45%. The weight ratio of surfactant to builder will generally be in the range of from 1:12 to 2:1.

In addition to builder and surfactant components, detergent formulations may contain fillers such as sodium sulfate and minor amounts of bleaches, dyes, optical brighteners, soil anti-redeposition agents, perfumes and the like.

In machine dishwashing compositions the surfactant will be a low-foaming nonionic or anionic, preferably nonionic surfactant which will constitute 0 to 5% of the formulation.

The term "low-foaming" surfactant connotes a surfactant which, in the foaming test described below, reduces the revolutions of the washer jet-spray arm during the wash and rinse cycles less than 15%, preferably less than 10%.

In the foaming test, 1.5 grams of surfactant is added to a 1969 Kitchen-Aid Home Dishwasher, Model No. KOS-16, manufactured by Hobart Manufacturing Company which is provided with means for counting revolutions of the washer jet-spray arm during wash and rinse cycles. The machine is operated using distilled water feed at a machine entrance temperature of 40°C. The number of revolutions of the jet-spray arm during the wash and rinse cycles is counted. The results are compared with those obtained by operation of the machine using no surfactant charge, and the percentage decrease in number of revolutions is determined.

The surfactant should, of course, be compatible with the chlorine containing component hereinafter discussed. Examples of suitable nonionic surfactants include ethoxylated alkyl phenols, ethoxylated alcohols (both mono- and di- hydroxy alcohols), polyoxyalkylene glycols, aliphatic polyethers and the like. The widely commercially utilized condensates of polyoxypropylene glycols having molecular weights of from about 1400 to 2200 with ethylene oxide (the ethylene oxide constituting 5 to 35 weight percent of the condensate) are, for example, advantageously used in the machine dishwashing formulations of this invention.

Suitable low-foaming anionic surfactants include alkyldiphenyl ether sulfonates such as sodium dodecyl diphenyl ether disulfonates and alkyl naphthalene sulfonates.

Mixtures of suitable low-foaming surfactants can be utilized if desired.

In addition, machine dishwashing formulations will contain sufficient chlorine providing compound to provide 0.5% to 2% available chlorine. For example, the formulation may contain from 0.5% to 5%, preferably 1% to 3% of a chlorocyanurate or from 10% to 30% chlorinated trisodium phosphate. Suitable chlorocyanurates are sodium and potassium dichlorocyanurate; [(monotrichloro) tetra-(monopotassium dichloro)] penta-isocyanurate; (monotrichloro) (monopotassium dichloro) diisocyanurate.

Machine dishwashing compositions should additionally contain from 5% to 30% soluble sodium silicate having an $SiO_2$ to $Na_2O$ mole ratio of from 1:1 to 3.2:1 preferably about 2.4:1 to inhibit corrosion of metal parts of dishwashing machines and provide over-glaze protection to fine china.

Machine dishwashing compositions will generally contain at least 10%, preferably at least 20% builder, up to a maximum of about 90% builder. The new builder compounds of this invention should constitute at least 5% of the weight of the machine dishwashing formulation in order to obtain the full effects of their inherent characteristics.

EXAMPLE I

Anhydrous trisodium carboxymethyloxysuccinate (850 grams) is blended with 150 grams water and heated to 117°C in a closed mixer. As the temperature rises, the mixture is converted from a damp powder to a smooth paste.

Stirring in continued for about 15 minutes while the temperature is allowed to drop to 113°C which results in crystallization of the mixture.

The mixer is opened and the temperature raised to 125°C to remove free water from the trisodium carboxymethyloxysuccinate monohydrate.

Table I, below, shows the characteristic X-ray diffraction pattern of the monohydrate as determined with a powdered sample using $CuK\alpha_1$ wavelength. For purposes of comparison, the X-ray diffraction patterns of the tetra and penta hydrates are also shown in Table I.

TABLE I

| MONOHYDRATE | | | TETRAHYDRATE | | | PENTAHYDRATE | | |
|---|---|---|---|---|---|---|---|---|
| $2\theta$ | d-spacing, A | $I/I°$ | $2\theta$ | d-spacing, A | $I/I°$ | $2\theta$ | d-spacing, A | $I/I°$ |
| 28.98 | 3.078 | 100 | 9.38 | 9.44 | 100 | 8.62 | 10.25 | 100 |
| 37.01 | 2.427 | 90 | 32.82 | 2.73 | 50 | 16.24 | 5.45 | 90 |
| 31.55 | 2.833 | 90 | 16.24 | 5.45 | 50 | 10.58 | 8.35 | 50 |
| 24.12 | 3.686 | 90 | 18.9 | 4.69 | 40 | 34.80 | 2.58 | 50 |
| 21.60 | 4.111 | 80 | 27.75 | 3.21 | 30 | 18.0 | 4.92 | <20 |
| 27.40 | 3.252 | 80 | 35.6 | 2.52 | 30 | 20.1 | 4.41 | <20 |
| 33.35 | 2.684 | 50 | 34.0 | 2.63 | 25 | 21.3 | 4.17 | <20 |
| 38.2 | 2.354 | 45 | 12.55 | 7.05 | <20 | 22.0 | 4.04 | <20 |
| 18.35 | 4.831 | 30 | 18.06 | 4.91 | <20 | 23.1 | 3.85 | <20 |
| 43.9 | 2.061 | 30 | 21.8 | 4.07 | <20 | 26.7 | 3.34 | <20 |

What is claimed is:
1. Crystalline trisodium carboxymethyloxysuccinate monohydrate.

* * * * *

UNITED STATES PATENT OFFICE
CERTIFICATE OF CORRECTION

Patent No. 3,965,169  Dated June 22, 1976

Inventor(s) N. Earl Stahlheber

It is certified that error appears in the above-identified patent and that said Letters Patent are hereby corrected as shown below:

Column 6, line 3, "in" should read -- is --.

Signed and Sealed this

Fifth Day of October 1976

[SEAL]

Attest:

RUTH C. MASON
Attesting Officer

C. MARSHALL DANN
Commissioner of Patents and Trademarks